United States Patent
Kiyota

(10) Patent No.: US 10,155,926 B2
(45) Date of Patent: Dec. 18, 2018

(54) MICROSCOPE APPARATUS AND CELL CULTURE APPARATUS

(71) Applicant: NIKON CORPORATION, Tokyo (JP)

(72) Inventor: Yasujiro Kiyota, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 15/389,591

(22) Filed: Dec. 23, 2016

(65) Prior Publication Data

US 2017/0101617 A1    Apr. 13, 2017

Related U.S. Application Data

(63) Continuation of application No. 12/923,004, filed on Aug. 27, 2010, now Pat. No. 9,562,215, which is a (Continued)

(30) Foreign Application Priority Data

Feb. 28, 2008 (JP) .................................. 2008-047270

(51) Int. Cl.
    C12M 1/00    (2006.01)
    G01N 1/31    (2006.01)
    (Continued)

(52) U.S. Cl.
    CPC ............ *C12M 41/14* (2013.01); *C12M 41/46* (2013.01); *G01N 1/312* (2013.01); (Continued)

(58) Field of Classification Search
    None
    See application file for complete search history.

(56) References Cited

U.S. PATENT DOCUMENTS 5,647,025 A * 7/1997 Frost .................. G02B 7/28
                                                250/201.3
2005/0013478 A1* 1/2005 Oba .................. G02B 21/0024
                                                382/154

(Continued)

FOREIGN PATENT DOCUMENTS

EP    1950789 A1 *  7/2008  .............. H01J 37/26
EP    2023127 A1 *  2/2009  .......... G01N 21/6458

(Continued)

OTHER PUBLICATIONS

Schormann, T. and Jovin, T. M., "Contrast Enhancement and depth perception in three-dimensional representation if differential interference contrast and confocal scanning laser microscope images.", J. Microscopy 166, pp. 155-168, (1992).*

(Continued)

*Primary Examiner* — James M Anderson, II
(74) *Attorney, Agent, or Firm* — Staas & Halsey LLP

(57) ABSTRACT

An imaging section of a microscope apparatus captures a plurality of microscope images each having the focal position which differs in the field being same with a light flux having passed through a microscopic optical system. A region separating section separates a cellular region from a non-cellular region by using the plurality of the microscope images. A focusing position calculating section finds a focusing position in a target pixel included in the cellular region based on a brightness change in the position being same in the plurality of the microscope images. A three dimensional information generating section generates three dimensional information of a cultured cell based on a position of the cellular region and the focusing position in the target pixel.

13 Claims, 5 Drawing Sheets

Related U.S. Application Data continuation of application No. PCT/JP2009/000308, filed on Jan. 27, 2009.

(51) Int. Cl.
  *G01N 35/00* (2006.01)
  *G02B 21/26* (2006.01)
  *G02B 21/36* (2006.01)
  *G02B 21/24* (2006.01)
  *C12M 1/34* (2006.01)

(52) U.S. Cl.
  CPC ....... *G01N 35/0099* (2013.01); *G02B 21/241* (2013.01); *G02B 21/26* (2013.01); *G02B 21/367* (2013.01)

(56) References Cited

U.S. PATENT DOCUMENTS

| | | | | |
|---|---|---|---|---|
| 2005/0105172 A1* | 5/2005 | Hasegawa | ............ | C12M 23/50 359/368 |
| 2006/0045505 A1* | 3/2006 | Zeineh | ............ | G02B 21/365 396/89 |
| 2007/0139657 A1* | 6/2007 | Ishimaru | ............ | G01B 11/2441 356/511 |
| 2008/0259443 A1 | 10/2008 | Smith et al. | | |
| 2009/0069893 A1 | 3/2009 | Paukshto et al. | | |

FOREIGN PATENT DOCUMENTS

| | | | | |
|---|---|---|---|---|
| JP | 63-66465 | 3/1988 | | |
| JP | 6-4601 | 1/1994 | | |
| JP | 8-294035 | 11/1996 | | |
| JP | 2001-281550 | 10/2001 | | |
| JP | 2003-29151 | 1/2003 | | |
| JP | 2003-501693 | 1/2003 | | |
| JP | 2005-55879 | 3/2005 | | |
| JP | 2006-23476 | 1/2006 | | |
| JP | 2007275030 A * | 10/2007 | ............ | C12M 41/46 |
| WO | 00/75709 A1 | 12/2000 | | |

OTHER PUBLICATIONS

International Preliminary Report on Patentability dated Sep. 10, 2010 in related International Patent Application No. PCT/JP2009/000308.

International Search Report dated Apr. 28, 2009 in related International Patent Application No. PCT/JP2009/000308.

Non-Final Office Action dated Jul. 31, 2012 in related U.S. Appl. No. 12/923,004.

Final Office Action dated Apr. 10, 2013 in related U.S. Appl. No. 12/923,004.

Advisory Action dated Sep. 30, 2013 in related U.S. Appl. No. 12/923,004.

Non-Final Office Action dated Oct. 25, 2013 in related U.S. Appl. No. 12/923,004.

Final Office Action dated Apr. 11, 2014 in related U.S. Appl. No. 12/923,004.

Non-Final Office Action dated Aug. 17, 2015 in related U.S. Appl. No. 12/923,004.

Final Office Action dated May 31, 2016 in related U.S. Appl. No. 12/923,004.

Notice of Allowance dated Sep. 26, 2016 in related U.S. Appl. No. 12/923,004.

U.S. Appl. No. 12/923,004, filed Aug. 27, 2010, Yasujiro Kiyota, Nikon Corporation.

* cited by examiner

MICROSCOPE APPARATUS AND CELL CULTURE APPARATUS

CROSS-REFERENCE TO RELATED APPLICATIONS

This application is a Continuation of: U.S. application Ser. No. 12/923,004, filed on Aug. 27, 2010, which is a Continuation Under 35 U.S.C. § 111(a), of PCT International Application No. PCT/JP2009/000308, filed Jan. 27, 2009, which claims the benefit of priority from Japanese Patent Application No. 2008-047270, filed on Feb. 28, 2008, the entire contents of which are incorporated herein by reference.

BACKGROUND

1. Field

The present application relates to a microscope apparatus and a cell culture apparatus.

2. Description of the Related Art

Until now, in order to analyze structures and functions of a cell, three dimensional information of the cell has been acquired by an observation using a microscope. As an example, Japanese Unexamined Patent Application Publication No. 2006-23476 discloses a configuration for acquiring three dimensional information by scanning a cell with a confocal laser scanning microscope.

However, when acquiring three dimensional information of a cell using a confocal laser scanning microscope as described above, the cell is damaged by the irradiation of excited light for a fluorescence observation, dyeing, etc., and therefore, there is room for improvement. In particular, the field of regenerative medicine is based on the premise that the cell cultured in vitro is implanted into a human body, and therefore, it is strongly required to acquire three dimensional information of a cell while suppressing the damage to the cell as much as possible.

DETAILED DESCRIPTION

Figure 1:
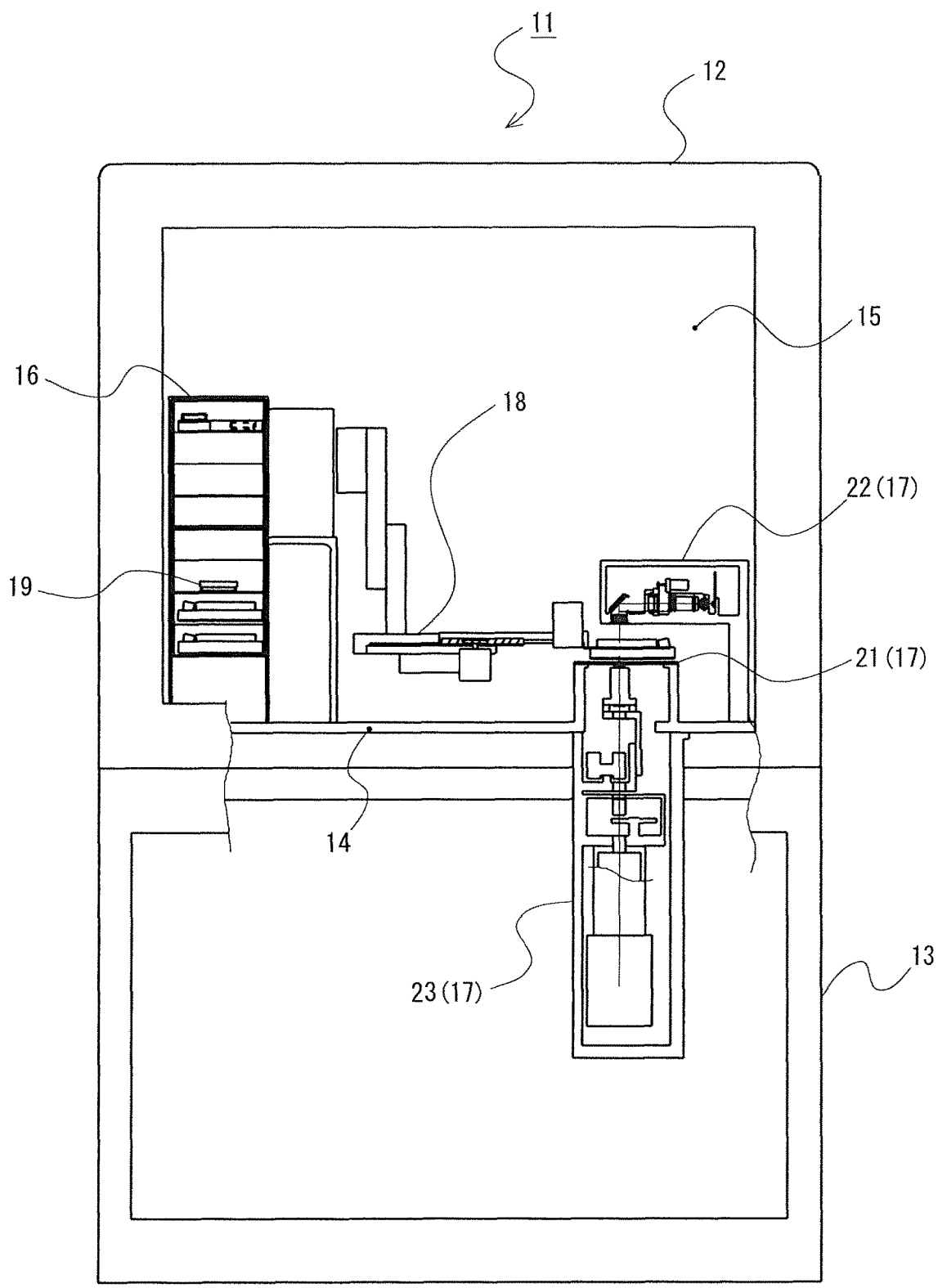
FIG. 1 is an elevation view of an outline of a cell culture apparatus in an embodiment.

A configuration of a cell culture apparatus in an embodiment will be explained below with reference to the drawings. FIG. 1 is an elevation view of an outline of a cell culture apparatus in the present embodiment.

A cell culture apparatus 11 in the present embodiment has an upper casing 12 and a lower casing 13. In an assembled state of the cell culture apparatus 11 shown in FIG. 1, the upper casing 12 is mounted on the lower casing 13. Meanwhile, the inner space of the upper casing 12 and the lower casing 13 is partitioned by a base plate 14 into an upper space and a lower space. Moreover, at the front of the cell culture apparatus 11, a door is provided to carry in/out a culture vessel 19 and mechanical equipment and materials (FIG. 1 shows a state where the door is open and for the sake of simplification, the door is not shown schematically).

Inside the upper casing 12, a temperature-controlled room 15 to culture a cell is formed. The temperature-controlled room 15 has a temperature adjusting device and a humidity adjusting device and the inside of the temperature-controlled room 15 is maintained to be an environment suitable for culturing a cell (for example, an atmosphere of a temperature of 37° C. and a humidity of 90%) (in FIG. 1, the temperature adjusting device and the humidity adjusting device are not shown schematically).

Furthermore, in the temperature-controlled room 15, a stocker 16, a microscope unit 17, and a vessel carrying device 18 are arranged.

The stocker 16 is arranged on the left side (left side in FIG. 1) of the temperature-controlled room 15 when viewed from the front of the upper casing 12. The stocker 16 has a plurality of shelves and it is possible to accommodate a plurality of the culture vessels 19 on each shelf of the stoker 16. Then, in each culture vessel 19, cells are placed along with the culture media.

The microscope unit 17 is arranged on the right side (right side in FIG. 1) of the temperature-controlled room 15 when viewed from the front of the upper casing 12. In the microscope unit 17, it is possible to make a time-lapse observation of a cell in the culture vessel 19.

The microscope unit 17 is fitted to and installed in an opening of the base plate 14 of the upper casing 12. The microscope unit 17 has a sample table 21, a stand arm 22 that extends over the sample table 21, and a main body part 23. While the sample table 21 and the stand arm 22 are arranged in the temperature-controlled room 15, the main body part 23 is placed in the lower caging 13. With such a configuration, it is made possible to make an observation of a cell in the culture vessel 19 with the environmental conditions unchanged.

Moreover, the sample table 21 is configured by a transparent material and the culture vessel 19 can be mounted thereon. The sample table 21 is configured so as to be capable of moving in the horizontal direction and of adjusting the position of the culture vessel 19 mounted on the top surface.

The vessel carrying device 18 is arranged in the center of the temperature-controlled room 15 when viewed from the front of the upper casing 12. The vessel carrying device 18 is configured by attaching arms for sandwiching the culture vessel 19 to the tip end of a vertical robot having articulated arms. Due to this, it is possible for the vessel carrying device 18 to deliver the culture vessel 19 with the stocker 16 and the sample table 21.

Next, the configuration of the microscope unit 17 in the present embodiment is explained with reference to FIG. 2. The microscope unit 17 has the above-mentioned sample table 21, a microscopic optical system (31 to 39), a lens driving section 24, an imaging section 25, a memory 26, and a control section 27. Here, the lens driving section 24, the memory 26, and the imaging section 25 are connected with the control section 27, respectively.

The microscopic optical system has a light source 31, a collector lens 32, a mirror 33, a field lens 34, a ring diaphragm 35 (aperture diaphragm), a condenser lens 36, an objective lens 37, a phase ring 38, and an image forming lens 39. Here, the light source 31, the mirror 33, the field lens 34, the ring diaphragm 35, and the condenser lens 36 are arranged in the stand arm 22. Moreover, the objective lens 37, the phase ring 38, and the image forming lens 39 are arranged in the main body part 23 (under the sample table 21).

Figure 2:
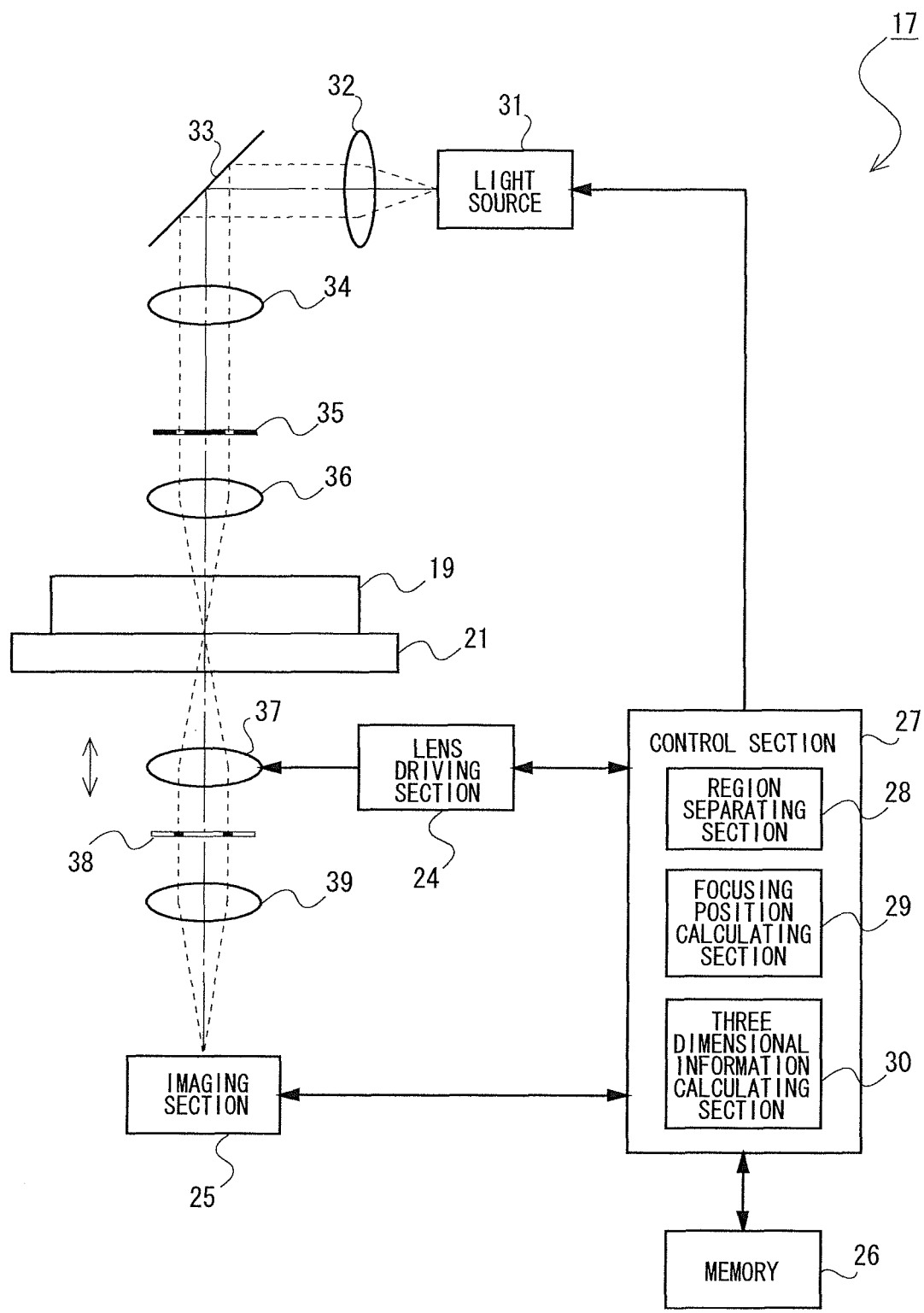
FIG. 2 is a schematic configuration diagram of a microscope unit in the present embodiment.

In FIG. 2, the illumination light emitted from the light source 31 becomes parallel light by the collector lens 32 and guided downward in FIG. 2 by the mirror 33. Then, the illumination light reflected from the mirror 33 is condensed by the field lens 34 and enters the ring diaphragm 35. The ring diaphragm 35 is a disc having a ring-shaped opening and turns the illumination light into light having passed through a ring-shaped diaphragm. The ring diaphragm 35 is arranged in the focal position on the front side of the condenser lens 36. Moreover, the condenser lens 36 condenses a light flux having passed through the ring diaphragm 35. In this way, the culture vessel 19 mounted on the sample table 21 is illuminated from above with the illumination light.

The objective lens 37 transmits the direct light (zero-order light) having passed through the culture vessel 19 and the diffracted light that is generated in accordance with a phase matter (a cultured cell) in the culture vessel 19. The phase ring 38 is arranged in a position optically conjugate to the ring diaphragm 35 in the focal point surface position on the rear side of the objective lens 37. The phase ring 38 transmits part of the diffracted light that is generated in the cultured cell and produces a delay (or advance) in the transmitted light phase. The image forming lens 39 forms an enlarged image of the cultured cell in the imaging section 25 based on the direct light and the diffracted light. In such a microscopic optical system, the light having passed through the phase ring 38 interferes with the light having passed through other than the phase ring 38, to form an image as a difference in brightness on an image forming surface via the image forming lens 39. In this way, it is possible to make a phase-difference observation of a cultured cell.

The lens driving section 24 adjusts the focal point of the microscopic optical system by driving the objective lens 37 in the direction of the optical axis (in the vertical direction in FIG. 2).

The imaging section 25 generates data of a microscope image by capturing an image formed by the microscopic observation system. The imaging section 25 has an image sensor, an analog front end that makes a gain adjustment for the output signal of the image sensor and performs A/D conversion, and an image processing section that performs various kinds of image processing. In FIG. 2, the individual components of the imaging section 25 are not shown schematically.

The memory 26 is configured by, for example, a nonvolatile storing medium, such as a flash memory. In the memory 26, data of a microscope image is stored. Moreover, in the memory 26, a program executed by the control section 27 is also stored.

The control section 27 is a processor that totally controls each part of the microscope unit 17. Further, the control section 27 functions also as a region separating section 28, a focusing position calculating section 29, and a three dimensional information calculating section 30 by executing the program stored in the memory 26. The explanation of the region separating section 28, the focusing position calculating section 29, and the three dimensional information calculating section 30 will be given later.

An example of the observation operation with the microscope unit 17 in the present embodiment will be explained below with reference to the flowchart in FIG. 3. In the example of the operation, the microscope unit 17 calculates the volume of a cultured cell in the field. In the example in FIG. 3, explanation is given on the premise that the culture vessel 19, which is an observation object, is in the state of being carried on the sample table 21 by the vessel carrying device 18. Meanwhile, in the culture vessel 19 shown in FIG. 4A, there are an attached cell and a floating cell in the culture solution.

Step S101: The control section 27 captures a plurality of microscope images with different focal positions in the same field range. Specifically, the control section 27 turns on the light source 31 to illuminate the culture vessel 19 and at the same time, captures a microscope image by driving the imaging section 25. After that, the control section 27 shifts the position of the objective lens 37 by the lens driving section 24 in the direction of optical axis (Z axis direction) and then repeats capturing a microscope image under the same shooting conditions. For example, a plurality of microscope images, sectioning of coordinates Z1 to Z5 of which is performed from the bottom toward the top of the culture vessel 19 is acquired. In this way, a plurality of microscope images with different focal positions in the same field is generated (refer to FIG. 4B). Here, the data of each microscope image captured in S101 is recorded in the memory 26 by the control section 27. It is assumed that the data of each microscope image is associated with focal position information indicative of the focal position of the objective lens 37 when the image is captured.

Step S102: The region separating section 28 finds a variance value of brightness of each pixel of the shooting screen corresponding to the microscope image by using a brightness value of a plurality of microscope images (S101). For example, the region separating section 28 calculates each variance value of brightness of all of the pixels of the coordinates (x, y) of the shooting screen from a plurality of brightness values indicated by the pixel of the coordinate (x, y) of each microscope image.

Step S103: The region separating section 28 separates a cellular region where a cultured cell is located from a non-cellular region where no cultured cell is located, based on the variance value of brightness (S102).

As an example, the region separating section 28 compares the variance value of brightness in the coordinates (x, y) of the shooting screen with a threshold value for determining a region. Here, in the position where a cultured cell is located on the shooting screen, the brightness changes between images due to the change in focal position. For this reason, in the position where a cultured cell is located, the variance value of brightness becomes larger. On the other hand, in the position where no cultured cell is located on the shooting screen, the brightness hardly changes between images even if the focal position changes. Accordingly, in the position where a cultured cell is located, the variance value of brightness becomes very small.

Consequently, when the variance value of brightness in the coordinates (x, y) is more than or equal to a threshold value, the region separating section 28 determines that the pixel in the coordinates (x, y) is in a cellular region. On the other hand, when the variance value of brightness is less than the threshold value, the region separating section 28 determines that the pixel in the coordinates (x, y) is in a non-cellular region. Then, the region separating section 28 separates the cellular region from the non-cellular region on the shooting screen by making the above-mentioned determination in each coordinate of the shooting screen. The state where the cellular region is separated from the non-cellular region on the shooting screen is shown schematically in FIG. 4B.

Additionally, in S103, the region separating section 28 performs grouping processing to group the pixels in the cellular region and labeling processing to associate each grouped cellular region with identification information (for example, identification number etc.) on one-on-one level.

Step S104: Further, the region separating section 28 sets a brightness threshold value by using the brightness value in the non-cellular region (S103). As an example, the region separating section 28 selects an arbitrary frame from among a plurality of microscope images (S101). Then, the region separating section 28 finds the above-mentioned brightness threshold value by averaging the brightness value of each pixel in the non-cellular region in the selected frame. The brightness threshold value found in S104 is used by the focusing position calculating section 29 when finding the focusing position in each pixel in the cellular region.

Step S105: The focusing position calculating section 29 finds the focusing position in each pixel in the cellular region (S103) of the shooting screen. This focusing position indicates the contour of a cell. That is, when a phase difference image (microscope image) is used, there is a characteristic that the larger the change in phase, the larger the brightness of the phase difference becomes in the region. For this reason, in general, the contour region of the cell has the maximum brightness. As an example, the focusing position calculating section 29 in S105 performs the following processing (1) to (3).

(1) The focusing position calculating section 29 selects a target pixel, which is a processing object, from among those in the cellular region of the shooting screen. Then, the focusing position calculating section 29 acquires the brightness value corresponding to the above-mentioned target pixel from the data (S101) of each microscope image.

(2) The focusing position calculating section 29 compares each brightness value acquired in the above-mentioned (1) with the brightness threshold value (S104). Here, in a pixel in which the change in brightness due to a phase difference appears in the direction of brightness, the relative brightness value is the largest when the objective lens 37 is in the focusing position. On the other hand, in a pixel in which the change in brightness due to a phase difference appears in the direction of darkness, the brightness value is relatively the smallest when the objective lens 37 is in the focusing position.

For this reason, when each brightness value acquired in the above-mentioned (1) is more than or equal to the brightness threshold value, the focusing position calculating section 29 performs the following processing. In this case, the focusing position calculating section 29 finds the maximum point of the brightness value in the spatial direction by using the brightness value acquired in the above-mentioned (1). Then, the focusing position calculating section 29 determines that the focal position of the objective lens 37 where the microscope image indicating the above-mentioned maximum point can be acquired is the focusing position in the target pixel. In this way, it is possible to find the focusing position in a pixel in which the change in brightness due to a phase difference appears in the direction of brightness.

On the other hand, when each brightness value acquired in the above-mentioned (1) is less than the brightness threshold value, the focusing position calculating section 29 performs the following processing. In this case, the focusing position calculating section 29 finds the minimum point of the brightness value in the spatial direction by using the brightness value acquired in the above-mentioned (1). Then, the focusing position calculating section 29 determines that the focal position of the objective lens 37 where the microscope image indicating the above-mentioned minimum point can be acquired is the focusing position in the target pixel. For this reason, it is possible to find the focusing position in a pixel in which the change in brightness due to a phase difference appears in the direction of darkness.

Meanwhile, in this (2), the focusing position calculating section 29 may extract a microscope image the brightness value of which is the maximum (or minimum) in the position of the target pixel and at the same time, may determine that the focal position of the objective lens 37 corresponding to the extracted microscope image is the focusing position. Alternatively, the focusing position calculating section 29 may find an interpolation curve that interpolates each brightness value in the position of the target pixel and at the same time, may find the focusing position of the objective lens 37 by calculation based on the maximum point (or minimum point) on the interpolation curve.

(3) The focusing position calculating section 29 changes the target image, which is a processing object, to another pixel, repeats the processing in the above-mentioned (2), and finds the focusing position of the objective lens 37 in each pixel in the cellular region. Then, the focusing position calculating section 29 generates a focusing position map indicating the focusing position of the objective lens 37 for each pixel in the cellular region of the shooting screen.

Figure 4A:
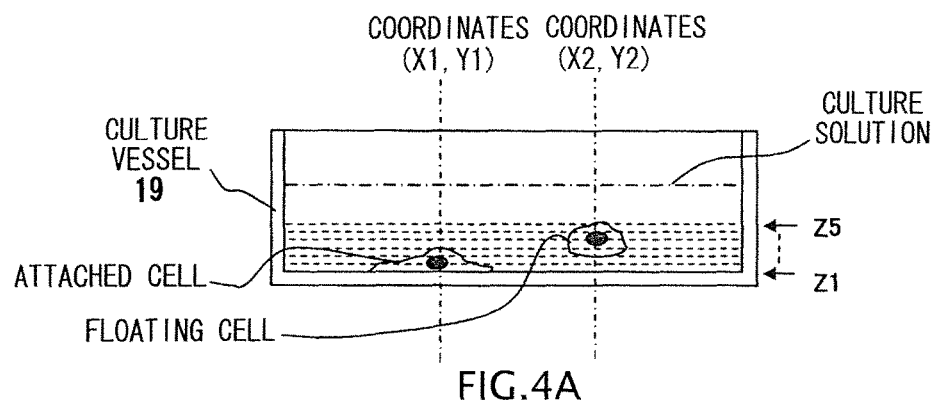
FIG. 4A is a diagram showing an example of a microscope image.
Figure 4B:
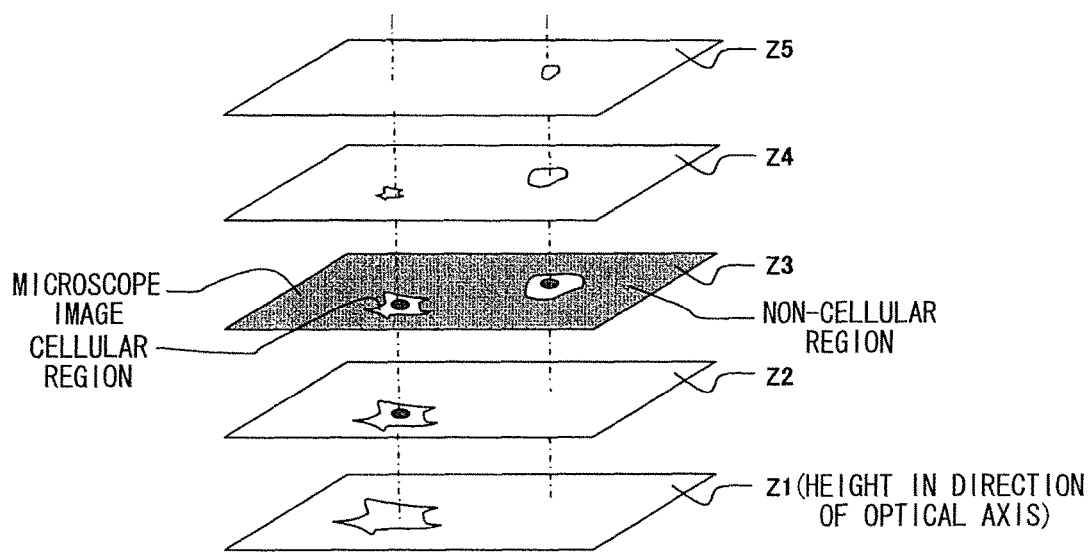
FIG. 4B is a diagram showing a state where a cellular region and a non-cellular region are separated in FIG. 4A.

Step S106: The three dimensional information calculating section 30 finds the height of the contour surface of the cultured cell (the position of the contour surface of the cultured cell in the direction of optical axis) based on the focusing position of the objective lens 37. That is, the three dimensional information calculating section 30 finds the height of the contour surface of the cultured cell corresponding to the position of the pixel from the focusing position (S105) of the objective lens 37 in each pixel by using the publicly-known optical fundamental expression (Gaussian formula of lens). In this way, it is possible for the three dimensional information calculating section 30 to obtain data of a three dimensional distance image (point group data) indicating the height of the contour surface of the cultured cell. A relationship between the height of the contour surface of the cultured cell and the focusing position in the example in FIG. 4A is shown in FIG. 5.

Step S107: The three dimensional information calculating section 30 determines which kind of a floating cell and an attached cell each cellular region grouped in S102 belongs to, based on the height of the contour surface of the cultured cell (S106).

Specifically, first, the three dimensional information calculating section 30 acquires the bottom position of the culture vessel 19. For example, the three dimensional information calculating section 30 regards the position where the height of the contour surface is the lowest as the bottom position of the culture vessel 19 in all of the cellular regions in the shooting screen (refer to FIG. 5). This is because the position of the contour surface corresponding to the above-mentioned condition can be thought to correspond to the outer edge of the attached cell attached to the bottom of the culture vessel 19.

Figure 5:
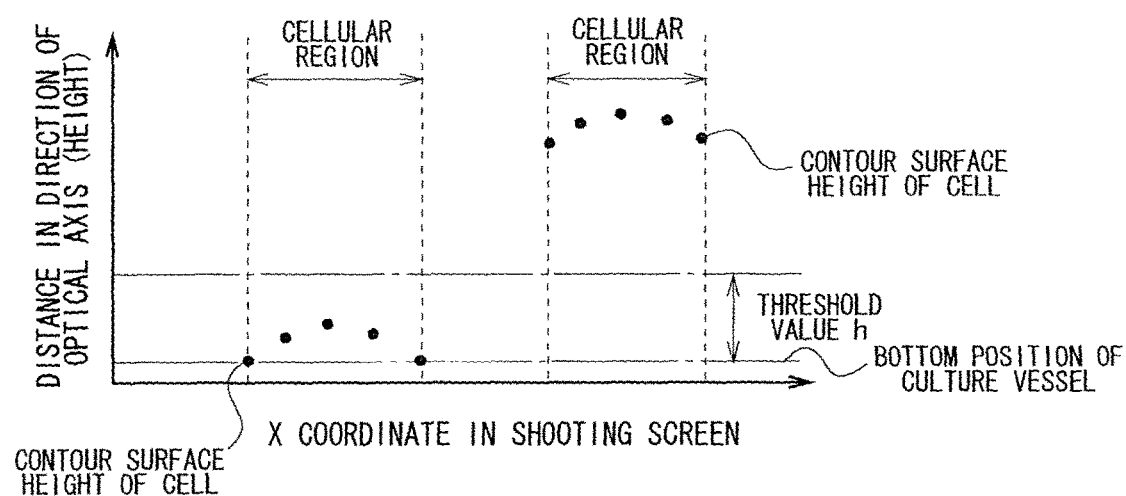
FIG. 5 is a diagram showing an example of a relationship between the height of a contour surface of a cultured cell shown in FIG. 4A and a focusing position.

Then, the three dimensional information calculating section 30 determines a cell, the contour surface height of which is a fixed distance (threshold value h) or more apart from the bottom position of the culture vessel 19 of the group of the cellular region, as a floating cell (refer to FIG. 5). In this way, it becomes possible for the three dimensional information calculating section 30 to automatically identify a floating cell and an attached cell in the shooting screen.

Step S108: The three dimensional information calculating section 30 estimates a total volume of attached cells included in the shooting screen. Specifically, first, the three dimensional information calculating section 30 excludes from processing objects those determined as a floating cell in step S107 in the cellular region of the shooting screen. Next, the three dimensional information calculating section 30 finds the area of a unit pixel by taking into account the magnification of the objective lens 37. Then, the three dimensional information calculating section 30 estimates the volume of each cultured cell by integrating the height (S106) of each pixel included in the cellular region (attached cell), which is a processing object. After that, the three dimensional information calculating section 30 generates data of the total volume of the attached cells included in the shooting screen and records it in the memory 26. With that, the explanation of the flowchart in FIG. 3 is completed.

The action and effect of the present embodiment will be explained below. The microscope unit 17 in the present embodiment finds each focusing position of the pixel in the cellular region by using a plurality of phase-difference observation images with different focal positions and acquires a three dimensional shape of the cultured cell based on the focusing position. Therefore, it is possible to acquire three dimensional information of the cultured cell without damaging the cell by the radiation of excited light or dyeing with the microscope unit 17 in the present embodiment. Further, with the microscope unit 17 in the present embodiment, the cultured cell is observed in the temperature-controlled room 15, and therefore, it is unlikely that the cultured cell is damaged by the change in the environmental conditions at the time of observation.

Moreover, the microscope unit 17 in the present embodiment finds three dimensional information of a cultured cell by using a plurality of phase-difference observation images after narrowing the cellular region in advance in the shooting screen. In this way, it is possible to alleviate the load of calculation when finding three dimensional information of the cultured cell with the microscope unit 17 in the present embodiment.

Further, with the microscope unit 17 in the present embodiment, it is possible to distinguish the floating cell from the attached cell and to estimate the volume of the cultured cell based on the three dimensional information of the cultured cell, and therefore, it is possible to further improve the functionality of the cell culture apparatus 11.

Figure 3:
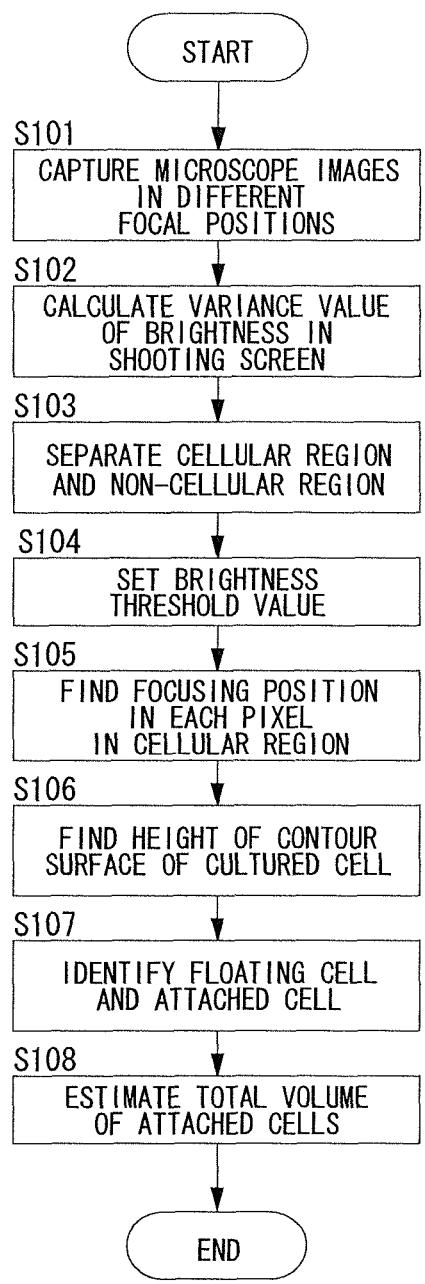
FIG. 3 is a flow chart for explaining an example of an observation operation with the microscope unit in the present embodiment.

In particular, when the time-lapse observation accompanied by a series of processes shown in FIG. 3 is made by using the cell culture apparatus 11 in the present embodiment, a growth curve can be obtained, which indicates the transition of the total volume of the attached cells over time. In this way, with the cell culture apparatus 11 in the present embodiment, it also becomes possible to accurately observe, for example, laminated cells, and evaluate the cultured state thereof.

Supplementary of the Embodiment (1) It may also be possible for the region separating section 28 in the above-mentioned embodiment to perform region separation only with the brightness value without using the variance value. Meanwhile, when the region separating section 28 performs region separation by using the variance value as in the above-mentioned embodiment, there is a merit that the contrast becomes stronger and it becomes easier to perform region separation.

(2) The microscope unit 17 in the above-mentioned embodiment may be a differential interference microscope that has a birefringence optical material on the focal surface on the side of the light source and on the focal surface on the side of the image and which forms an image by converting a phase difference of a sample into a brightness difference by interference of light waves (the optical system of a differential interference microscope is publicly known, and therefore, its detailed explanation is omitted and not shown schematically).

(3) The operation of the microscope unit 17 in the above-mentioned embodiment is merely an example and the processing shown in FIG. 3 may be combined appropriately and performed. As an example, the microscope unit 17 may omit the operation in S107 and find the volume of all the cells included in the shooting screen. Alternatively, it may be configured such that the microscope unit 17 performs only the processing to distinguish the floating cell from the attached cell. That is, the microscope unit 17 may complete the series of processes without performing the processing in S108 after the operation in S107.

(4) The configuration of the microscope unit 17 in the above-mentioned embodiment is merely an example. For example, the microscope unit 17 of the present invention may have a configuration in which the light source 31 is arranged under the sample table 21 and on the other hand, the objective lens 37, or the like is arranged above the culture vessel 19. Further, the microscope apparatus of the present invention is not limited to that arranged in the temperature-controlled room 15 and it is obvious that a microscope apparatus used outside the temperature-controlled room 15 is also included in the technical scope of the present invention.

(5) It may be configured such that the microscope unit 17 in the above-mentioned embodiment adjusts the focal point by driving the position of the sample table 21, instead of the objective lens 37, in the direction of optical axis.

(6) The algorithm to find the volume of the cultured cell is not limited to the example in the above-mentioned embodiment. As an example, it may be configured such that the three dimensional information calculating section 30 approximately calculates the volume of each grouped cultured cell by approximating the area of the cellular region with other shapes, such as a rectangle and a circle, and multiplying the height at an arbitrary position of the cellular region (or the average height in the cellular region).

(7) In the above-mentioned embodiment, although the example in which each function of the region separating section 28, the focusing position calculating section 29, and the three dimensional information calculating section 30 is realized by software, that is, programs, is explained, it may also be possible to realize these components by hardware by using ASIC.

(8) Meanwhile, the programs stored in the memory 26 in the above-mentioned embodiment may be firmware programs that are updated by upgrading etc. That is, it may also be possible to provide the functions of the microscope apparatus of the present invention by updating the firmware programs of an already existing microscope apparatus.

The many features and advantages of the embodiment are apparent from the detailed specification and, thus, it is intended by the appended claimed to cover all such features and advantages of the embodiment that fall within the true spirit and scope thereof. Further, since numerous modifications and changes will readily occur to those skilled in the art, it is not desired to limit the inventive embodiment to the exact construction and operation illustrated and described, and accordingly all suitable modifications and equivalents may be resorted to, falling within the scope thereof.

What is claimed is:

1. A microscope apparatus comprising:
a microscopic optical system;
an imaging section capturing, along an optical axis of the microscopic optical system, a plurality of images at different focal positions, the plurality of images including a cell;
a calculating section calculating height information of the cell in a direction of the optical axis of the microscopic optical system based on the different focal positions and a brightness value of pixels in the same position of the plurality of images in the direction of the optical axis, the calculating section finding a focusing position of the cell from a pixel having the maximum or minimum brightness value among the pixels in the same position of the plurality of images, and generating a height of a contour surface of the cell as the height information by using the found focusing position of the cell; and
a determining section determining whether the cell is a floating cell or an attached cell based on the height information, the determining section determining a cell having equal or higher contour surface height than a threshold value as the floating cell, and determining a cell having a shorter contour surface height than the threshold value as the attached cell.

2. The microscope apparatus according to claim 1, wherein
the threshold value is a fixed distance apart from a basic height which is the lowest height of the contour surface.

3. The microscope apparatus according to claim 1, wherein
the calculating section calculates a volume of the attached cell by using three dimensional information including the height information.

4. The microscope apparatus according to claim 1, wherein
the imaging section captures the plurality of images in the same field by adjusting a distance between the cell and a focal position of the microscopic optical system in the direction of the optical axis.

5. The microscope apparatus according to claim 1, wherein:
the microscopic optical system is capable of performing a phase-difference observation of the cell; and
the plurality of images include a phase difference image.

6. The microscope apparatus according to claim 1, wherein:
the microscopic optical system is capable of performing a differential interference observation of the cell; and
the plurality of images include a differential interference image.

7. A method for acquiring height information of a cell comprising:
capturing, along an optical axis of the microscopic optical system, a plurality of images at different focal positions, the plurality of images including a cell;
calculating height information of the cell in a direction of the optical axis of the microscopic optical system based on the different focal positions and a brightness value of pixels in the same position of the plurality of images in the direction of the optical axis the calculating including:
finding a focusing position of the cell from a pixel having the maximum or minimum brightness value among the pixels in the same position of the plurality of images; and
generating a height of a contour surface of the cell as the height information by using the found focusing position of the cell; and
determining whether the cell is a floating cell or an attached cell based on the height information, the determining including determining a cell having equal or higher contour surface height than a threshold value as the floating cell, and determining a cell having a lower contour surface height than the threshold value as the attached cell.

8. The method according to claim 7, wherein
the threshold value is a fixed distance apart from a basic height which is the lowest height of the contour surface.

9. The method according to claim 7, further comprising
calculating a volume of the attached cell by using three dimensional information indicating the height information.

10. The method according to claim 7, further comprising
capturing the plurality of images in the same field by adjusting a distance between the cell and a focal position of the microscopic optical system in the direction of the optical axis.

11. The method according to claim 7, wherein:
the microscopic optical system is capable of performing a phase-difference observation of the cell; and
the plurality of images include a phase difference image.

12. The method according to claim 7, wherein:
the microscopic optical system is capable of performing a differential interference observation of the cell; and
the plurality of images include a differential interference image.

13. A non-transitory computer readable storage medium to store a program causing a computer to execute:
capturing, along an optical axis of the microscopic optical system, a plurality of images at different focal positions, the plurality of images including a cell;
calculating height information of the cell in a direction of the optical axis of the microscopic optical system based on the different focal positions and a brightness value of pixels in the same position of the plurality of images in the direction of the optical the calculating including:
finding a focusing position of the cell from a pixel having the maximum or minimum brightness value among the pixels in the same position of the plurality of images; and
generating a height of a contour surface of the cell as the height information by using the found focusing position of the cell; and
determining whether the cell is a floating cell or an attached cell based on the height information, the determining including determining a cell having equal or higher contour surface height than a threshold value as the floating cell, and determining a cell having a lower contour surface height than the threshold value as the attached cell.

* * * * *

UNITED STATES PATENT AND TRADEMARK OFFICE
CERTIFICATE OF CORRECTION

PATENT NO. : 10,155,926 B2  
APPLICATION NO. : 15/389591  
DATED : December 18, 2018  
INVENTOR(S) : Yasujiro Kiyota Page 1 of 1

It is certified that error appears in the above-identified patent and that said Letters Patent is hereby corrected as shown below:

In the Claims

In Column 10, Line 2:
In Claim 7, delete "axis" and insert -- axis, --, therefor.

In Column 10, Line 48:
In Claim 13, delete "optical" and insert -- optical axis, --, therefor.

Signed and Sealed this
Nineteenth Day of March, 2019

Andrei Iancu
*Director of the United States Patent and Trademark Office*